United States Patent [19]

Cartwright et al.

[11] Patent Number: 5,288,633
[45] Date of Patent: Feb. 22, 1994

[54] **PSEUDOMONAS CEPACIA STRAIN 5.5B AND METHOD OF CONTROLLING *RHIZOCTONIA SOLANI* THEREWITH**

[75] Inventors: D. Kelly Cartwright; D. Michael Benson, both of Cary, N.C.

[73] Assignee: North Carolina State University, Raleigh, N.C.

[21] Appl. No.: 923,857

[22] Filed: Jul. 31, 1992

[51] Int. Cl.$^5$ .......................... C12N 1/20; C12N 1/00
[52] U.S. Cl. ................................. 435/253.3; 435/874
[58] Field of Search .......... 424/93 N; 435/254, 252.4, 435/874, 253.3

[56] References Cited

U.S. PATENT DOCUMENTS

| | | | |
|---|---|---|---|
| 4,535,061 | 8/1985 | Chakrabarty et al. | 435/253 |
| 4,588,584 | 5/1986 | Lumsden et al. | 424/93 |
| 4,642,131 | 2/1987 | Hoitink | 435/252.4 |
| 4,798,723 | 1/1989 | Dart et al. | 435/874 |
| 4,880,745 | 11/1989 | Kijima et al. | 435/254 |
| 4,900,348 | 2/1990 | Hoitink | 435/252.4 |
| 4,975,277 | 12/1990 | Janisiewicz et al. | 424/93 |
| 4,998,586 | 1/1991 | Toyoda et al. | 424/93 |

FOREIGN PATENT DOCUMENTS

| | | |
|---|---|---|
| 0350244A2 | 1/1990 | European Pat. Off. . |
| 0472492A2 | 2/1992 | European Pat. Off. . |
| 3291578 | 11/1988 | Japan ............................. 424/93 N |
| WO90/01327 | 2/1990 | PCT Int'l Appl. . |

OTHER PUBLICATIONS

Adams; G. C., *Advances in Plant Pathology*, chap. 36, Academic Press, 1988, pp. 535-552.
Renato DeFreitas et al., "Pseudomonas cepacia and Pseudomonas putida as Winter Wheat Inoculants for Biocontrol of *Rhizoctonia solani*," *Can. J. Microbiol.*, vol. 37, (1991).
Homma, Y., et al., "Soil Biol. Biochem.," vol. 21(5), 1989, pp. 723-728.
Renato DeFreitas, et al., "Plant Growth Promoting rhzobacteria for winter wheat," *Can. J. Microbiol.*, 36:265-272, 1990.
Rothrock, C. S., et al., "Role of Antibiosis in antagonism of *Streptemyces hygroscopicus* var. geldanus to *Rhzoctonia solani* in soil," *Can. J. Microbiol.*, 30:1440-1447, 1984.

*Primary Examiner*—Douglas W. Robinson
*Assistant Examiner*—Kristin Larson
*Attorney, Agent, or Firm*—Bell, Seltzer, Park & Gibson

[57] ABSTRACT

An isolated *Pseudomonas cepacia* strain having the identifying characteristics of *Pseudomonas cepacia* NCSU strain 5.5B (A.T.C.C. No. 55,344) is disclosed. Also disclosed are a biocontrol agent comprising the aforementioned strain and a method of controlling Rhizoctonia comprising the step of administering such a biocontrol agent in an amount sufficient to inhibit the growth of *Rhizoctonia solani*.

1 Claim, 7 Drawing Sheets

PSEUDOMONAS CEPACIA STRAIN 5.5B AND METHOD OF CONTROLLING RHIZOCTONIA SOLANI THEREWITH

FIELD OF THE INVENTION

This invention relates generally to the biocontrol of Rhizoctonia solani in plants, and relates more specifically to the use of a novel strain of Pseudomonas cepacia as a biocontrol agent for Rhizoctonia solani in plants.

BACKGROUND OF THE INVENTION

Rhizoctonia stem rot is a condition of plants in which Rhizoctonia solani Kuhn [Teleomorph = Thanatephorus cucumeris (Frank) Donk], colonizes in the stem and roots of a plant. Stem rot is a serious disease which can result in stunting or die back of mature plants later in production. Jones, R. K., North Carolina Flower Growers' Bulletin, 35(4):6-11 (1990); Strider, D. L. et al., Poinsettias in Diseases of Floral Crops Volume 2, 351-403 (D. L. Strider, ed., Praeger Publishers, New York, 1985). Stem rot can be detrimental during all stages of plant growth, but is particularly favored under the conditions that prevail during late-summer rooting. Consequently, the prevention or control of stem rot during the rooting period is critical. Ecke, P., Jr., Matkin, O. A., and Hartley, D. E. (eds). The Poinsettia Manual. (Paul Ecke Poinsettias. Encinitas, Calif., 1990).

Control of stem rot is dependent on cultural practices and the use of effective chemical fungicides. Powell, C. C., Jr., Plant Dis 72:693-695 (1988); Snowden, S. E. et al., Fungic and Nematic Tests 38:182 (1982). The use of clean, sterilized pots, pasteurized soil or propagation medium, disease free stock plants, and sanitary greenhouse practices combined with repeated applications of fungicides such as benomyl [(methyl 1-(butylcarbamoyl)-2-benzimidazole-carbamate] or PCNB (pentachloronitrobenzene) can reduce severity and spread of stem rot. See Snowden et al., supra, Bolton, A. T., Canadian J Plant Path. 5:181-184 (1983). The disease, however, continues to occur annually at endemic and occasionally epidemic levels. This is attributed to poor management, time, labor, and expense involved in the implementation of control measures and growing fears and constraints related to chemical pesticide use. See Tweedy, B. G, The future of chemicals for controlling plant diseases in Challenging Problems in Plant Health 405-415 (T. Kommedahl and P. H. Williams, eds. The American Phytopathological Society. St. Paul, Minn. 1983); see also Urbain, C. D., Farm Jour 110(13):15-16 (1986). For example, fungicides, particularly when misused, can pose environmental and health related risks. Food and groundwater contamination, residue carryover, applicator exposure, plant injury, and buildup of pest resistance due to pesticides have cast doubts about their future use. See Urbain, supra; Staub, T. et al., Plant Dis 68(12):1026-1031 (1984); Powell, C. C., Jr., Plant Dis 72:693-695 (1988).

These problems have stimulated interest in alternative means of disease control, such as biological control. Cook, R. J. et al., Perspectives in The Nature and Practice of Biological Control of Plant Pathogens 426-444 (R. J. Cook and K. F. Baker, eds., American Phytopathological Society, St. Paul, Minn. 1983); Baker, K. F., The future of biological and cultural control of plant disease in Challenging Problems in Plant Health 422-430 (T. Kommedah. and P. H. Williams, eds., American Phytopathological Society, St. Paul, Minn. 1983). Biological control of plant diseases with antagonistic microorganisms has potential; these tactics can be safe, effective, and economical. Efforts to control R. solani with strains of fungi, bacteria, or actinomycetes have shown marginal success; however, none have been developed for use on a practical basis. See Beagle-Ristaino, J. E. et al., Phytopathology 75:560-564 (1985); Kwok, O. C. H. et al., Phytopathology 77:1206-1212 (1987); Rothrock, C. S. et al., Can. J. Microbiol 30:1440-1447 (1984).

Accordingly, it is an object of the present invention to provide a method for treating stem rot of plants through the use of a biocontrol agent. It is a further object to provide the aforementioned biocontrol agent.

SUMMARY OF THE INVENTION

These and other objects are satisfied by the present invention, which as a first aspect includes an isolated Pseudomonas cepacia strain having the identifying characteristics of Pseudomonas cepacia NCSU strain 5.5B (A.T.C.C. No. 55,344).

The present invention includes as a second aspect a biocontrol agent for controlling Rhizoctonia diseases caused by Rhizoctonia solani comprising an isolated Pseudomonas cepacia strain having the identifying characteristics of Pseudomonas cepacia NCSU strain 5.5B (A.T.C.C. No. 55,344). In a preferred embodiment, the biocontrol agent includes a nutrient-containing solution which is capable of sustaining growth of the Pseudomonas cepacia but incapable of sustaining growth of the Rhizoctonia solani.

A third aspect of the present invention is a method of combatting Rhizoctonia solani in plants comprising administering a biocontrol agent comprising an isolated Pseudomonas cepacia strain having the identifying characteristics of Pseudomonas cepacia NCSU strain 5.5B (A.T.C.C. No. 55,344) to a plant in an amount effective to inhibit the growth of Rhizoctonia solani. In a preferred embodiment, the biocontrol agent includes a nutrient-containing solution which is capable of sustaining growth of Pseudomonas cepacia but is incapable of sustaining growth of Rhizoctonia solani.

FIG. 9B is a plot of *R. solani* colonization as a function of time on the entirety of root cubes inoculated with subcultured and rifampicin- resistant *P. cepacia.*

FIG. 10A is a plot of *P. cepacia* population survival rate as a function of time in root cubes infested with *R. solani* for samples of *P. cepacia* stored at 20° C. (5.5BW) and samples stored at 4° C. (5.5BWC).

FIG. 10B is a plot of *R. solani* colonization as a function of time on the entirety of root cubes inoculated with *P. cepacia* samples stored at 20° C. (5.5BW) and samples stored at 4° C. (5.5BWC).

DETAILED DESCRIPTION OF THE INVENTION

The present invention is directed at a novel strain of *Pseudomonas cepacia* and its use as a biocontrol agent in the control of stem rot caused by *Rhizoctonia solani.*

The isolated strain of *Pseudomonas cepacia* is a novel strain having the identifying characteristics of *Pseudomonas cepacia* NCSU strain 5.5B (A.T.C.C. No. 55,344). This strain was deposited with the American Type Culture Collection, 12301 Parklawn Drive, Rockville, Md. 20852 USA, on 23 Jul. 1992 under the provisions of the Budapest Treaty and will be irrevocably and without restriction or condition released to the public upon the issuance of a patent.

Strain 5.5B was uncovered it uncultivated soil around Raleigh, N.C. It may be found in open soil, rhizosphere soil, or on the roots of existing plants. The bacterium is a gram negative rod, generally bearing flagella for motility. As determined by MIDI (Newark, Del. 19711), the fatty acid profile for the bacteria resembles that of other *Pseudomonas cepacia* strains. Strain viability can be tested by streaking on agar plates.

The strain can be isolated by known techniques of bacterial isolation, such as the serial dilution of soil containing the bacterium in water followed by streaking on agar. Exemplary agars suitable for streaking include potato dextrose agar (PDA) (available from Difco Laboratories, Detroit, Mich.), V8+ agar (described in Dhingra et al., *Basic Plant Pathology Methods* 299 (CRC Press, Boca Raton, Fla.)) nutrient agar, (available from (NA) Difco Laboratories, Detroit, Mich.) and King's B agar (KB) (described in Dhingra et al., supra at 313).

Pure cultures of the bacterium can be maintained on suitable agar media, such as PDA, NA, KB, and diluted PDA agar. As used herein, a "biologically pure culture" means a culture which contains primarily only bacteria from the 5.5B strain and which is substantially free of other contaminating bacteria. The cultures can be maintained and stored at any temperature at which it remains viable; a temperature range of between about 0° C. and 30° C. is suitable for maintenance and storage.

The present invention also includes a biocontrol agent comprising *Pseudomonas cepacia* NCSU 5.5B strain for controlling Rhizoctonia diseases caused by *Rhizoctonia solani.* The biocontrol agent can be in the form of a biologically pure culture and can include an agriculturally acceptable carrier, such as water, in which the bacteria can survive.

The biocontrol agent of the present invention preferably includes an aqueous nutrient solution to help sustain growth of the *Pseudomonas cepacia* 5.5B strain. A preferred nutrient solution comprises PDA, and more preferably comprises PDA diluted with water. Also preferred is a nutrient solution which will sustain growth of the *Pseudomonas cepacia* 5.5B strain but will not sustain the growth of *Rhizoctonia solani.*

*The Pseudomonas cepacia* 5.5B strain should be present in the biocontrol agent in an amount and at a concentration sufficient for inhibiting the growth of *Rhizoctonia solani.* A preferred concentration of *Pseudomonas cepacia* 5.5B is between about $1\times10^4$ and $1\times10^{12}$ cells/ml of solution; a more preferred concentration of *Pseudomonas cepacia* is between about $1\times10^6$ and $1\times10^9$ cells/ml. Concentrations in this range are capable of controlling and even halting the infestation of *Rhizoctonia solani* in plants.

The biocontrol agent can be stored at any temperature at which the *Pseudomonas cepacia* 5.5B strain remains alive and viable. Exemplary storage temperatures are between about 0° C. and 30° C.; a preferred storage temperature range is between about 0° C. and 10° C.

The biocontrol agent of the present invention can be used to combat Rhizoctonia diseases in a wide variety of plants. The term "plant" is used herein in a generic sense, and encompasses woody-stemmed plants such as trees and shrubs. Plants to be treated with the biocontrol agent and methods described herein include whole plants and any portions thereof, such as field crops, potted plants, cut flowers, and harvested fruits and vegetables. Plants prone to Rhizoctonia stem rot are described in Farr et al., *Fungi on Plants and Plant Products in the United States.* 932-933 (American Phytopathological Society, St. Paul, Minn. 1983), the contents of which are hereby incorporated herein by reference.

Ornamental plants which may be treated by the biocontrol agent of the present invention include potted ornamentals such as azalea (Rhododendron spp.), hydrangea (*Macrophylla hydrangea*), aloe (Aloe spp.) hybiscus (*Hybiscus rosasanensis*), and cut flowers such as roses (Rosa spp.), tulips (Tulipa spp.), daffodils (Narcissus spp.), petunias (*Petunia hybrids*), carnations (*Dianthus caryophyllus*), and poinsettias (*Euphorbia pulcherima*). Treatment with the biocontrol agent can prolong life of the plant and improve its appearance. Preferably, the biocontrol agent is used to combat *Rhizoctonia solani* in poinsettia. Fruits and vegetables that can be treated by the method of the present invention include tomatoes (*Lycopersicon esculentum*), lettuce (e.g., *Lactuca sativa*), soybean (*Glycine max*), green beans (*Phaseolus vulgaris*), lima beans (*Phaseolus limensis*), peas (Lathyrus spp.), sorghum (sorghum spp.), members of the genus Cucumis such as cucumber (*C. sativus*), cantaloupe (*C. cantalupensis*), and musk melon (*C. melo*), citrus fruits (citrus spp.), and members of the genus Coffea.

The present invention also includes a method of combatting *Rhizoctonia solani* in plants. The method comprises the step of administering a biocontrol agent comprising an isolated *Pseudomonas cepacia* strain having the characteristics of *Pseudomonas cepacia* NCSU strain 5.5B (A.T.C.C No. 55,344) to a plant in an amount sufficient to inhibit the growth of *Rhizoctonia solani.*

The bacterium can be administered to the plant in any manner that permits 5.5B to colonize on or around the plant. Administration can comprise direct application of the bacterium onto the plant itself, preferably onto the stem, or can comprise application of the medium in which the plant is growing, such as soil, root cubes, water, and the like. The administration step can be carried out in any fashion known to be an effective method of biocontrol agent application, such as dipping, spraying, brushing, and the like. In addition, the agent may be incorporated into other agents used to treat the plants, such as water, fertilizer, pesticide, fungicide, or other treatment.

The bacterium may be accompanied by a nutrient which is capable of sustaining growth of *Pseudomonas cepacia*. Exemplary nutrients include PDA, WA, and NA. Preferably the nutrient additive is a nutrient which is not capable of sustaining growth of *Rhizoctonia solani*.

The method of the present invention can further comprise the step of heating a culture of *Pseudomonas cepacia* 5.5B to at least 100° C. prior to the administration step. This step has the effect of killing the bacterium present in the suspension, but testing indicates that this step does not reduce the inhibition of Rhizoctonia by *Pseudomonas cepacia*.

The present invention is more completely illustrated by the following non-limiting examples. As used herein, "ml" means milliliters, "L" means liters, "g" means grams, "cm" means centimeters, "mm" means millimeters, "CFU" means colony forming units, and "hr" means hours.

EXAMPLE 1

Preparation of Stock Plants

Poinsettia stock plants [Gutbier V-14 Glory(red)] were maintained in potting media (Metromix 220) (Grace Sierra, Milpitas, Calif. 95035) contained in 6 L plastic pots on greenhouse benches. This cultivar was used for all subsequent experiments. Plants were fertilized weekly with a commercial 20-20-20 (N-P-K) fertilizer (2.7 g/L). Magnesium sulfate (2.4 g/L) was applied as a drench each month. Every three months, soil drenches of potassium nitrate (0.45 g/L), calcium nitrate (1.6 g/L) and a foliar spray of 1% molybdenum were applied. Stock plants were occasionally pruned back to facilitate new growth.

EXAMPLE 2

Collection and storage of *P. cepacia* 5.5B Isolate

Soil and plant samples were collected from ten different sites from February to June, 1991. These included samples from cultivated fields, undisturbed sites, and greenhouses in the Raleigh, N.C. area and from greenhouses in Charlotte, N.C.

Soil was serially diluted (1:10 dilutions) in sterile distilled water. A 0.1 ml aliquot from $10^{-2}$ to $10^{-5}$ dilutions was spread onto V8+ agar [200 ml V8 juice, 800 ml distilled water, 16 g agar, and 50 mg chlortetracycline], one-half strength potato dextrose agar [19.5 g Difco PDA, 3.75 g agar, 1000 ml distilled water, and 50 mg chlortetracycline] (0.5 PDA+), nutrient agar [23 g Difco nutrient agar and 1000 ml distilled water] (NA), and/or King's B agar [20 g proteose peptone, 2.5 g $K_2HP)4$, 15 ml glycerol, 6 g $MgSO_4$, 15 g agar, and 1000 ml distilled water] (KB).

To assay rhizosphere soil, plant roots were shaken vigorously to remove excess soil, placed in 90 ml of sterile distilled water and agitated for 30 minutes on a wrist action shaker. A 0.1 ml aliquot from this was spread onto media described.

Root sections (1-3 cm) were surface sterilized (95% ethanol for 1 minute), rinsed in sterile, distilled water (i minute), and plated onto media described. All plates were incubated on a laboratory bench.

Pure cultures were maintained on NA and/or KB, and were stored by suspension in sterile, distilled water in screw-top glass test tubes at 20° C. and 4° C.

EXAMPLE 3

In Vitro Visual Screening of *P. cepacia* 5.5B Isolate for Antagonism Against *R. solani*

Cells of isolate 5.5B prepared in Example 2 were streaked onto one side of a PDA plate. After several days of growth, a 7 mm diameter mycelia plug taken from the edge of an actively growing colony of *R. solani* (Isolate RS-3 from poinsettia) was placed opposite the isolate colony (about 1 cm distance). Plates were monitored daily and inhibition of *R. solani* growth was rated as either slight, moderate, or severe based on visual observation.

Observation indicated that *P. cepacia* 5.5B proved to be an effective isolate for in vitro inhibition of *R. solani* which suggested that it be tested further in greenhouse trials.

EXAMPLE 4

In vitro Screening of *P. cepacia* 5.5B Isolate for Antagonism Against *R. Solani*

*P. cepacia* 5.5B isolate was tested for in vitro inhibition against *R. solani* in the following way: 5.5B was streaked onto one side of a PDA plate, a water agar plate (20 g Difco agar, 1000 ml distilled water) (WA), and 0.13% PDA plate (1.3 g Difco PDA, 14.5 g agar, 1000 ml water) (WPDA). Plates were incubated on a laboratory bench for 14 days. A 7-mm-diameter plug taken from the margin of an actively growing colony of *R. solani* was placed opposite the 5.5B colony (1 cm distance). Plates were incubated at room temperature. Radial growth of *R. solani* was measured daily for three days and compared to control plates (*R. solani* alone on each the three media types). Three plates (replications) were used for each isolate and controls. The experiment was repeated once. Data were pooled and computer-analyzed with PC SAS using PROC ANOVA (SAS Institute, Cary, N.C.).

Figures 1, 2:
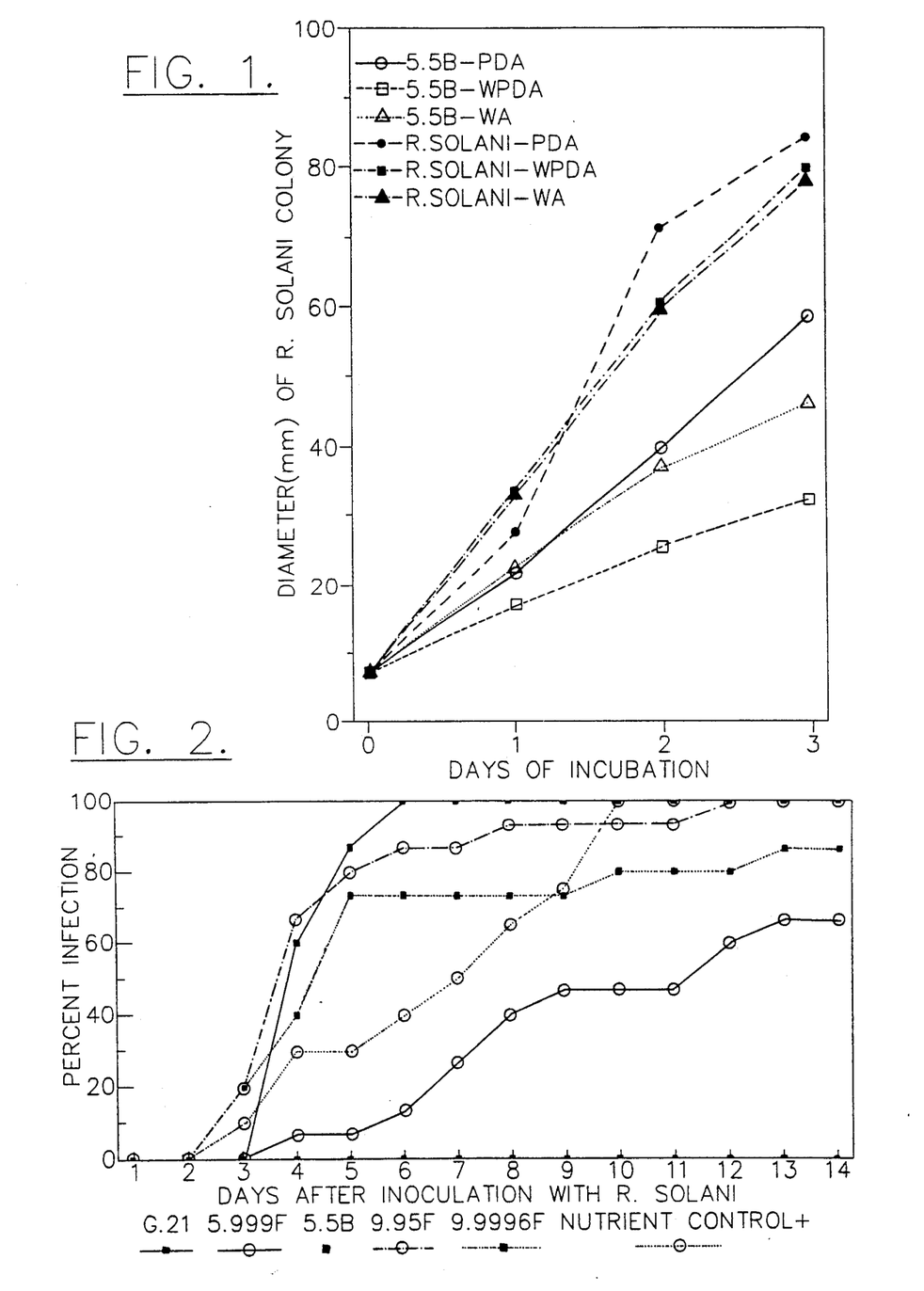
FIG. 1 is a plot of the diameter of R. solani colonies as a function of incubation time for treated and untreated samples.
FIG. 2 is a plot of the infection percentage of poinsettias as a function of time for treated and untreated samples.

The data indicate that the degree of in vitro inhibition of *R. solani* by isolate 5.5B varied depending on the type of media. The most restriction occurred on 0.13 percent PDA where, after zero, one, two, and three days of growth, colony diameter of *R. solani* was 7, 17, 25.7, and 32.5 mm, respectively (FIG. 1). Colony diameter of *R. solani* on PDA after day zero, one, two, and three was 7, 21.8, 40.2, and 59 mm; colony diameter of *R. solani* in WA was and 7, 22.7, 37.5, and 46.3 mm for the same time increments. Colony diameter of *R. solani* growing unrestricted on PDA, 0.13 percent PDA, and WA after three days ranged from 7 to 85, 7 to 80.3, and 7 to 78.5, respectively (FIG. 1). Thus in general, 5.5B isolate did exhibit inhibitory activity against *R. solani*.

EXAMPLE 5

Initial Greenhouse Screening of *P. cepacia* 5.5B Isolate

*P. cepacia* 5.5B isolate was grown on PDA for 10 to 14 days. Inoculum was prepared by blending one colony mat (the colony plus the PDA contained in petri dish) with cells only from one to two additional colonies in 160 ml of sterile distilled water in a Waring blender at high speed for 45 to 60 seconds. The resultant suspension was filtered through one layer of cheesecloth.

Inoculum of R. solani was prepared by seeding twice autoclaved rice contained in 250 ml flasks (25 g rice/19 ml distilled water) with two mycelial plugs taken from the margin of an actively growing colony of R. solani. Flasks were incubated on a laboratory bench for 4 to 9 days.

Two strips (two cubes/strip) of rooting cubes (Oasis Rootcubes, Smithers-Oasis, Kent, Ohio) were soaked in antagonist inoculum and fitted with a styrofoam sleeve secured with two rubber bands (two cubes served as one replication, with two replications/treatment). About 18 to 24 hours after soaking, a rice grain colonized by R. solani was placed on the top center surface of each of the two cubes. Cuttings between 5 and 8 cm in length taken from stock plants described in Example 1 were placed in cube holes on each side of the rice grain and immediately misted. A watering regime of one minute of mist/hour 14 times a day was used during all test periods. Infested and uninfested cuttings soaked in sterile, distilled water and PDA nutrient based solution served as controls.

Infection progress (number of plants infected/day) and mortality of plants were monitored for 14 days. Cuttings were rated for disease severity based on the following scale: "1"=no stem lesion; "2"=lesions on less than 25% of stem; "3"=lesions covering between 26 and 50% of stem; "4"=lesions covering between 51 and 75% of stem; and "5"=stem completely girdled or collapsed.

Results (Table 1) obtained during early greenhouse trials demonstrated that the 5.5B isolate was sufficiently efficacious to merit further screening in greenhouse tests.

TABLE 1

Initial Greenhouse Screening of Biocontrol Agents for Rhizoctonia Solani on Polyfoam Rooting Cubes

| Treatments[a] | Disease Rating[b] |
|---|---|
| 5.5 B | 1.0 |
| 5.1 F | 4.0 |
| 7.6 F | 2.0 |
| 8.5 B | 2.0 |
| 6.3 B | 2.0 |

[a]Treatments: 5.5 B = Pseudomonas cepacia strain 5.5 B; 8.5 B, 6.3 B = unidentified bacterial isolates 5.1 F, 7.6 F = unidentified fungal isolates
[b]Disease rating on poinsetta cuttings after two weeks.

EXAMPLE 6

Greenhouse Assessment of P. cepacia 5.5B Control of R. solani

Isolate 5.5B was streaked onto PDA and incubated at room temperature for 10 to 14 days. Inoculum was prepared by blending a single colony mat plus cells from two to three additional colonies of each isolate in 600 ml of sterile, distilled water in a Waring blender for 45 to 60 seconds. The solution was filtered through one layer of cheesecloth. This formulation consisted of approximately 0.13% PDA.

Cubes were soaked in inoculum and incubated on greenhouse benches. About 18 to 24 hr after soaking, a rice grain infested with R. solani was placed on the top center surface of each cube and at either end. Poinsettia cuttings were positioned in the cubes. Three replications with five cubes per replication were used for each treatment. Three infested and three uninfested cuttings soaked in sterile, distilled water served as unnourished controls, and three infested and three uninfested cuttings soaked in a 0.13% solution of PDA served as nutrient controls.

Infection progress and mortality were monitored daily for 14 days. Disease severity was rated based on the scale previously described in Example 5. Root development was evaluated as follows: "0"=plant dead; "1"=plant healthy or diseased but alive, no root initials present; "1.5"=beginning of root initial formation; "2"=distinct root initials; "2.5"=callus tissue completely encircling the stem; "3"=callus tissue plus beginning of lateral roots; and "3.5"=callus plus distinct lateral roots. No rooting data was taken for plants with a disease severity rating of five.

Experimental design was a randomized completed block. Consistent results were obtained during three complete experiments with application of the isolate. Computer analysis of variance was performed with PC SAS by PROC ANOVA or GEM for individual trials. Means were separated with the Waller-Duncan K-Ratio test.

Infection progress was rapid on poinsettia cuttings in controls infested with R. solani. Infection typically appeared three to five days after inoculation and progressed rapidly, typically resulting in plant death five to seven days later (FIG. 2). Infection appeared to be faster in nutrient based infested controls, although progress was rapid in cubes soaked in water only. However, isolate 5.5B demonstrated significant and consistent control of R. solani infestation over repeated trials (FIG. 2). No infection or mortality was noted for plants in cubes treated with isolate 5.5B.

Root development in the 5.5B treatments was not significantly different from untreated controls in other trials. The root development rating for 5.5B during these tests was 2.6.

EXAMPLE 7

The Effect of Inoculum Concentration of Isolate 5.5B on Efficacy of R. solani Control Inoculum for isolate 5.5B was obtained by streaking cells from a subculture of 5.5B onto Potato Dextrose Agar (PDA) and incubating plates at room temperature on a laboratory bench. Inoculum was prepared as previously described in Example 5. The population density for the inoculum was determined by serial dilution techniques to be $2.6 \times 10^9$ CFU/ml. This initial suspension was diluted in 0.13% PDA solution in 1:10 increments to produce solutions 10, 100, 1000, and 10,000 times more dilute than the original inoculum. Both infested and uninfested controls of water or 0.13% PDA solution were included in all tests. Infection and mortality of plants were monitored daily. Disease and root development were assessed at the end of two weeks. Root development was examined only for plants with a disease rating of less than 4.

Figure 3:
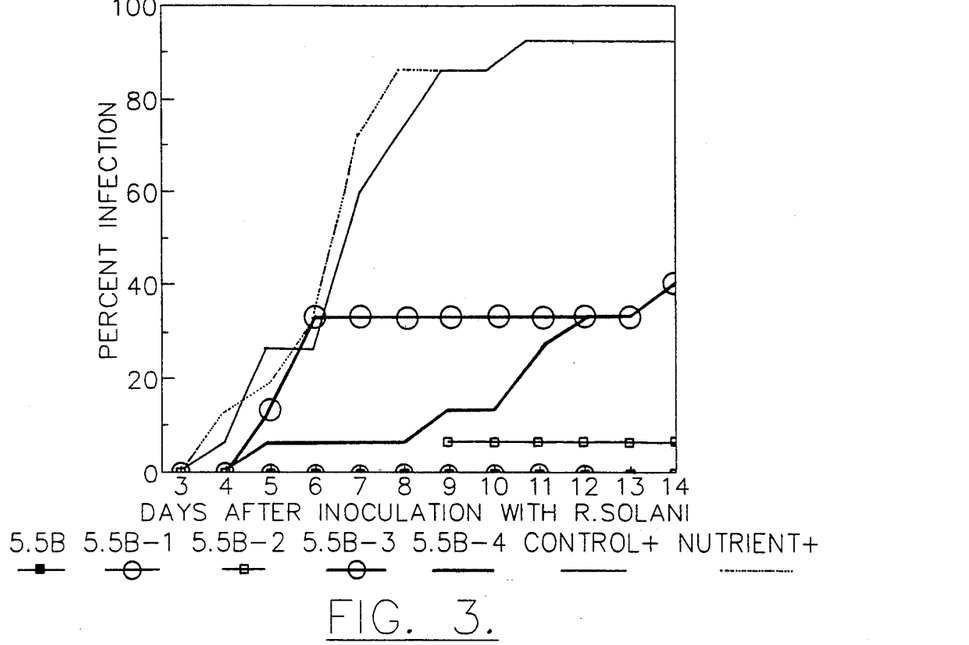
FIG. 3 is a plot of the infection percentage of poinsettias as a function of time for treated samples varying in concentration of P. cepacia.

The results obtained are shown in FIG. 3. No infection was observed in any experiment with any undiluted treatment of 5.5B. Generally, infection (FIG. 3) and mortality (data not shown) increased as the inoculum became more dilute, with infection percentage values increasing from 0 to 40 percent with dilution and mortality values increasing from 0 to 33 percent. Cuttings in the infested controls developed disease rapidly.

Root development (data not shown) was lower in all experiments than that seen in uninfested water controls, but was similar to that of uninfested nutrient controls.

EXAMPLE 8

Effect of Isolate 5.5B on Radial growth of *R. solani* In Vitro

Cells from isolate 5.5B (from subculture) were streaked at four corners of 9 cm petri dishes containing PDA, WPDA (0.13% PDA), or WA (water agar) and allowed to grow for 10 days. A 5 mm mycelial disk of *R. solani* was placed in the center of the plate of each medium. As a control, a 5 mm mycelial disk of *R. solani* was placed in the center of each of the three media without antagonists. The diameter (mm) of the colony of *R. solani* was measured for three days for each treatment. Data are reported as the average diameter of the colony of *R. solani* for each treatment at each day.

Figure 4:
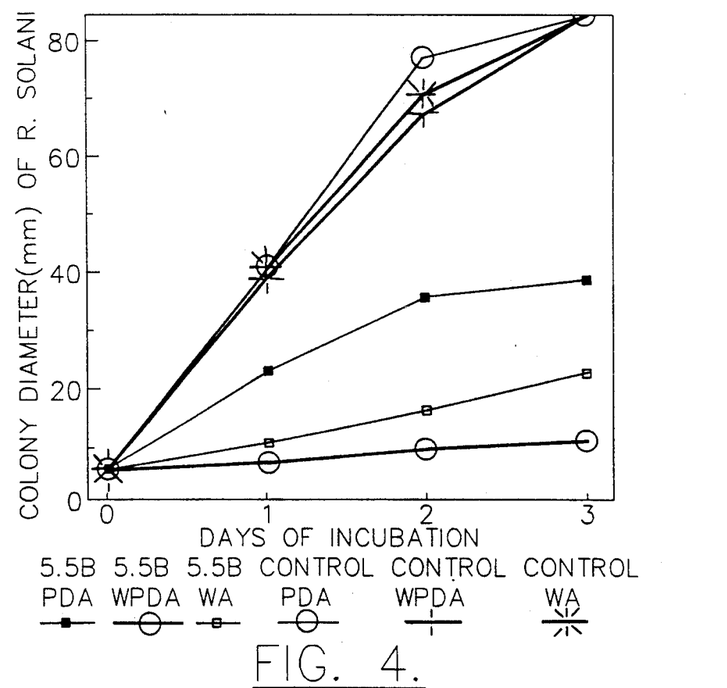
FIG. 4 is a plot of the colony diameter of R. solani as a function of time for treated and untreated samples grown on differing nutrient media.

As shown in FIG. 4, isolate 5.5B restricted *R. solani* the most on WPDA, followed by WA and PDA. The average colony diameter of *R. solani* challenged with isolate 5.5B was 11.3, 6.7, and 8.7 mm on PDA, WPDA, and WA after one day; 21.7, 7, and 9.3 mm after two days; and 27.6, 7.3, and 11 mm after three days. Average diameter of *R. solani* in unchallenged treatments was 29, 22.7, and 26.3 mm on PDA, WPDA, and WA after one day; 63.7, 47.7, and 54 mm after two days; and 85, 85, and 71.5 mm after three days.

COMPARATIVE EXAMPLE A

Efficacy of Known Antagonists of *R. solani*, *Gliocladium virens* (G6) and *Pseudomonas Fluorescens* (PF5) Compared to Isolate 5.5B for Control of *R. solani* on Poinsettia Isolates G6 and PF5 were obtained from the United States Department of Agriculture in College Station, Tex. All isolates were grown on PDA on a laboratory bench at room temperature for 12-14 days. Inocula for isolates G6, PF5, and 5.5B were prepared as described previously in Example 5 in a 0.13% PDA solution. Conidial concentration of G6 was determined with a hemacytometer to be about $4 \times 10^7$ conidia per ml. Cell concentrations of 5.5B and PF5 were determined by serial dilution to be about $4 \times 10^9$ cells/ml and $4 \times 10^7$ cells/ml, respectively. Each of the inocula was applied to rooting cubes in the manner described in Example 6 Poinsettia cuttings were placed in the cubes and observed for mortality and infection.

Figure 5:
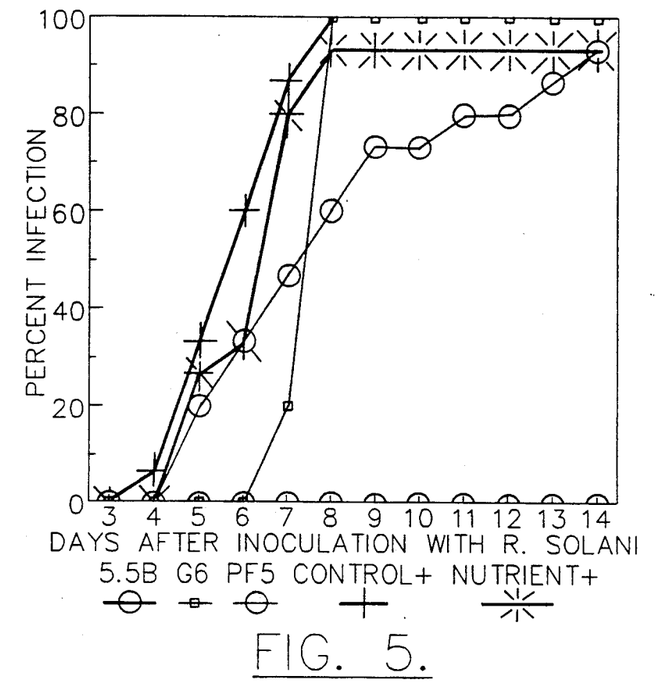
FIG. 5 is a plot of the infection percentage of poinsettias as a function of time for P. cepacia treated samples as compared to other known biocontrol agents.

As shown in FIG. 5, no infection occurred in the 5.5B-treated cubes. One hundred percent of poinsettias in cubes treated with G6 were infected and died within 14 days. Infection for PF5 treated poinsettias was 93.3 percent, and mortality for PF5 treated plants was 86.7 percent (data not shown). Infection for the infested controls ranged from 80-100 percent. Infection in the G6 and PF5 treated cubes and the infested controls developed after 4-6 days and progressed rapidly within 2-3 days thereafter, with greater than 80% infection observed (FIG. 6A). No control of *R. solani* was exhibited by either G6 or PF5.

It was observed that the inoculum concentration for PF5 was lower than that of 5.5B in these two tests. In an additional trial, however (data not shown), in which concentration of PF5 was raised to $2 \times 10^8$ cells/ml, infection and mortality were 93.3% and 93.3%, respectively, which indicates that PF5 does not control *R. solani* in this system.

The root development rating of cuttings in the 5.5B treatments was 1.5. This value compares favorably with values of 1.8 and 1.33 obtained for the uninfested water and nutrient controls. The cuttings, for the most part, appeared healthy despite the less developed root system.

EXAMPLE 9

Effect of Nutrient vs. Nutrient-free Inoculum of Isolate 5.5B and Methods of Storage on Efficacy to Control *R. solani* on Poinsettia in Polyfoam Rootcubes Isolate 5.5B was grown on PDA at room temperature on a laboratory bench for 12-15 days. Nutrient-containing inoculum was prepared in a 0.13% PDA solution by blending colony mats and colonies of 5.5B as previously described. Nutrient-free inoculum (5.5BN-) was obtained by rinsing colonies of isolate 5.5B from agar surface with sterile distilled water and blending without agar.

In addition, several methods of storage of these isolates were tested to examine any differences in efficacy related to storage. Table 2 describes treatment designation, type of storage from which inoculum was proliferated, and inoculum concentration of isolate 5.5B.

TABLE 2

| Treatment | Description/Method of Storage | Concentration (CFU/ml) |
|---|---|---|
| 5.5 B | Inoculum grown from subcultures | $2 \times 10^9$ |
| 5.5 BN— | Same as above except inoculum prepared without nutrients | $1.75 \times 10^9$ |
| 5.5 BW | Inoculum grown by starting cultures from cultures stored in water at 20° C. in the dark | $1.2 \times 10^9$ |
| 5.5 BWN— | Same as above except inoculum prepared without nutrients | $2.03 \times 10^9$ |

Figure 6:
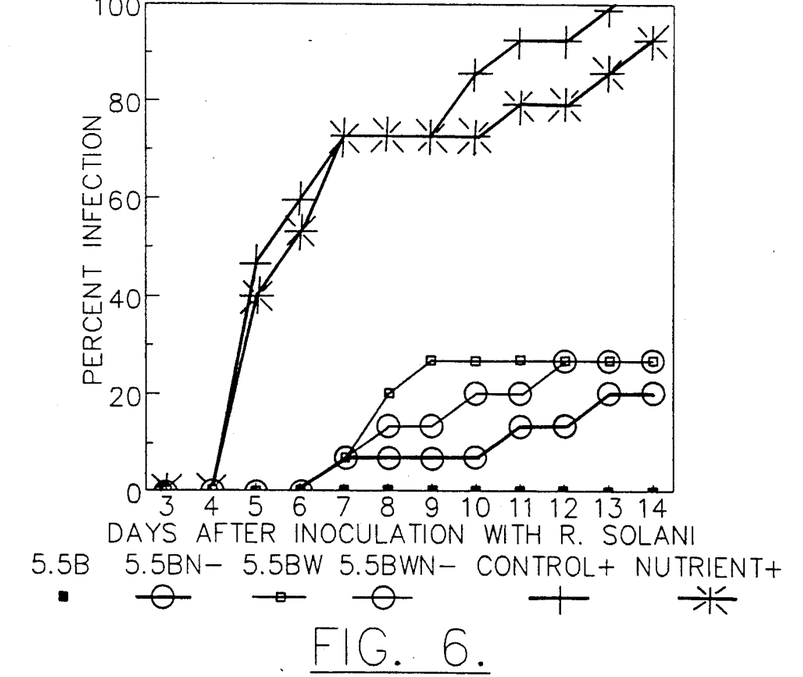
FIG. 6 is a plot of the infection percentage of poinsettias as a function of time for nutrient-containing and nutrient free P. cepacia samples.

FIG. 6 shows that the effect of nutrients on efficacy of control of *R. solani* was slight with all treatments utilizing 5.5B. No infection was observed with treatment 5.5B (nutrient-based) compared to 20% and 13.3% for the nutrient-free treatment of 5.5B in experiment three.

The effect of storage conditions of isolate 5.5B on efficacy of control was also minimal. For the nutrient-based treatments 5.5B and 5.5BW, infection percentages were 0 and 26.7%, respectively, while infection percentages for nutrient-free treatments 5.5BN-and 5.5BWN- were 20 and 26.7 percent, respectively. Mortality percentages for the nutrient-based treatments were 0 (5.5B) and 26.7 (5.5BW) percent, while the mortality percentages for the nutrient-free treatments were 13.3 (5.5BN-) and 20 (5.5BWN-) percent (data not shown). Disease onset in treatments of all variations of 5.5B was typically delayed by 2-4 days.

Root development was less than in the uninfested controls. Values for root development ratings ranged from 1.47 to 1.86 for all treatments of 5.5B. Root development for the uninfested controls ranged from 1.9-2.07.

EXAMPLE 10

Effect of Autoclaved Suspensions of Isolate 5.5B Incorporated into Media on Radial Growth of *R. solani*

A colony of isolate 5.5B was grown from a previously prepared subculture of isolate 5.5B. After 14 days, inoculum was prepared as previously stated by blending one colony mat plus three additional colonies in 600 ml of sterile distilled water and filtering through cheesecloth. Concentration of the 5.5B suspension was $1 \times 10^9$ CFU/ml. After preparation, inoculum was allowed to set overnight at room temperature. After 24 hr, the suspension was diluted with distilled water to the following concentrations of PDA: 1) No dilution (original inoculum=0.13% PDA); 2) 0.065% PDA; 3) 0.043% PDA; and 4) 0.0325% PDA. Controls consisted of suspensions of the above mentioned concentrations of PDA as well as full strength PDA without the antagonist. Fifteen g of agar/L was added to the dilutions. After diluting, each suspension was autoclaved at 121° C,. for 20 minutes, cooled, and poured into 9 cm petriplates. A 7 mm mycelial plug of R. solani was placed in the center of each plate/treatment. Radial growth of R. solani was measured daily for three days.

Figure 7:
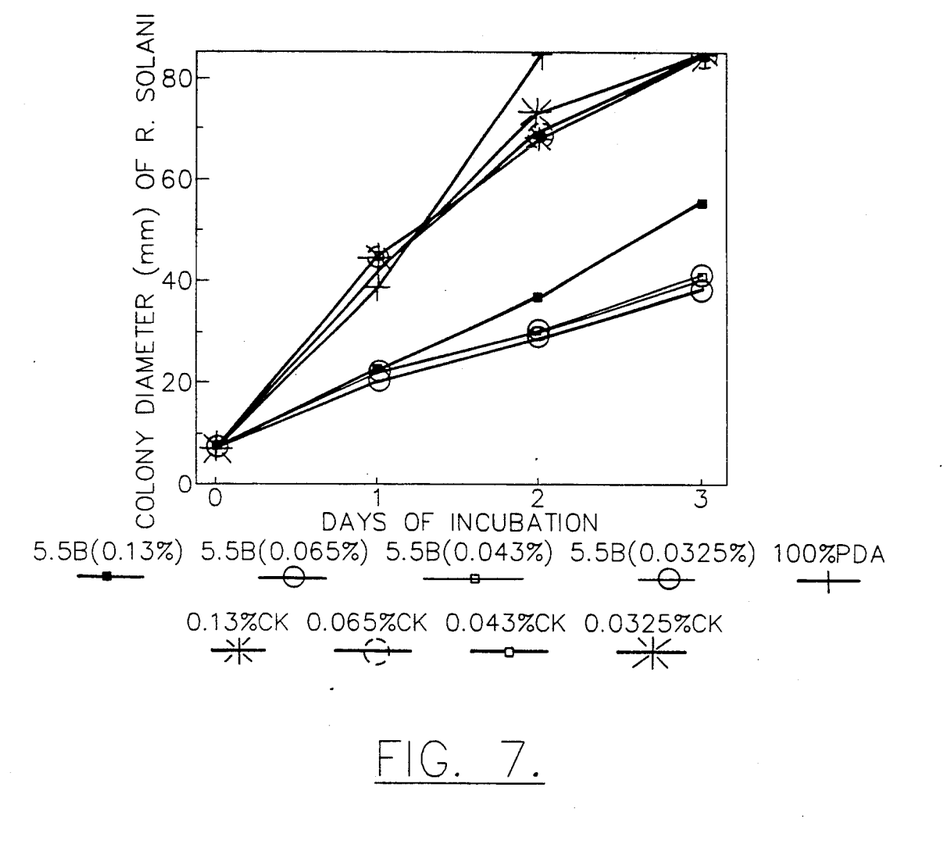
FIG. 7 is a plot of the colony diameter of R. solani colonies as a function of time for samples of P. cepacia autoclaved at 121° C. and diluted to specific nutrient contrations prior to incorporation into media.

FIG. 7 indicates that incorporating autoclaved cells of isolate 5.5B into the medium restricted growth of R. solani. The least restriction of R. solani occurred with the undiluted inoculum treatment (0. 13% PDA) . In each control plate, the colony of R. solani grew to the edge of the plate (85 mm) after three days.

EXAMPLE 11

Relation of Colonization by R. solani and Population Dynamics of Isolate 5.5B in Polyfoam Rooting cubes Containing Poinsettias and Inoculated with R. solani Inoculum for the population studies was grown using water stored cultures of 5.5B. Several methods of producing inoculum from these sources were tested to determine any differences in efficacy or population fluctuations. A rifampicin resistant strain of isolate 5.5B was also used to aid in selection of the bacterium from the rooting cubes. Table 3 describes designations for samples of inoculum produced by different preparation methods.

TABLE 3

| Treatment | Description |
|---|---|
| 5.5 BW | Grown from cultures stored in water at 20° C. in the dark. |
| 5.5 BSW | Subcultured one time from cultures grown from water stored cultures |
| 5.5 BR | Rifampicin resistant strain generated using 100 mg rifampicin/L of media |
| 5.5 BWC | Grown from cultures stored in water at 4° C. in the dark |

All isolates were grown on PDA at room temperature for 13-15 days. Inoculum preparation was consistent with methods previously described in Example 5 in 0.13% PDA. Population of 5.5BR was determined by serial dilution and plating onto King's B medium plus rifampicin (100 mg/L)[KB+R]. Population of 5.5B was determined by plating dilutions onto KB. Colonies of 5.5B obtained from cube assays were recognized by colony color, shape, and growth pattern. In some of the experiments, all other types of bacteria in the 5.5B treatment were counted and population determined.

Application procedures of inoculum to cubes were consistent with those previously described in Example 6. Four replications with five cubes per replication (20 total plants) were used in a randomized complete block design. Data collection for infection, mortality, and root development were taken after three weeks and methods and scales were consistent with those previously described.

Methods for determining population of isolates and colonization of cubes by R. solani were as follows: One cube per replication was sampled on day 3, 7, 14, and 21 after soaking cubes with the antagonist. A total of 16 cubes per treatment were sampled during the three week period. For population determination, the cubes were first cut in half. Each half cube per replication per treatment was weighed (1 gm wet weight of cube contains 1 ml of water), and enough sterile distilled water was added to make 200 ml of solution (i.e. 178 ml of water added to 22 g of cube). The cube and water were then blended at high speed for 30 seconds. Dilutions were made from blended suspension and plated on appropriate media described.

Colony counts were made 48-72 hr later and population of isolate 5.5B in CFU's per ml (based on ml of water contained in cube) was determined. These values could then be compared to initial population of CFU's per ml. Population of isolate 5.5B was recorded as the percentage of initial population remaining ($I/I_o \times 100$; where $I$=population and $I_o$=initial population) or actual CFU's per ml remaining (plotted on a semi-log scale) after 3, 7, 14, or 21 days.

In some experiments, CFU's per ml of bacteria other than isolate 5.5B present in the cube were calculated and plotted in conjunction with antagonist population on a semi-log scale.

Figure 9A:
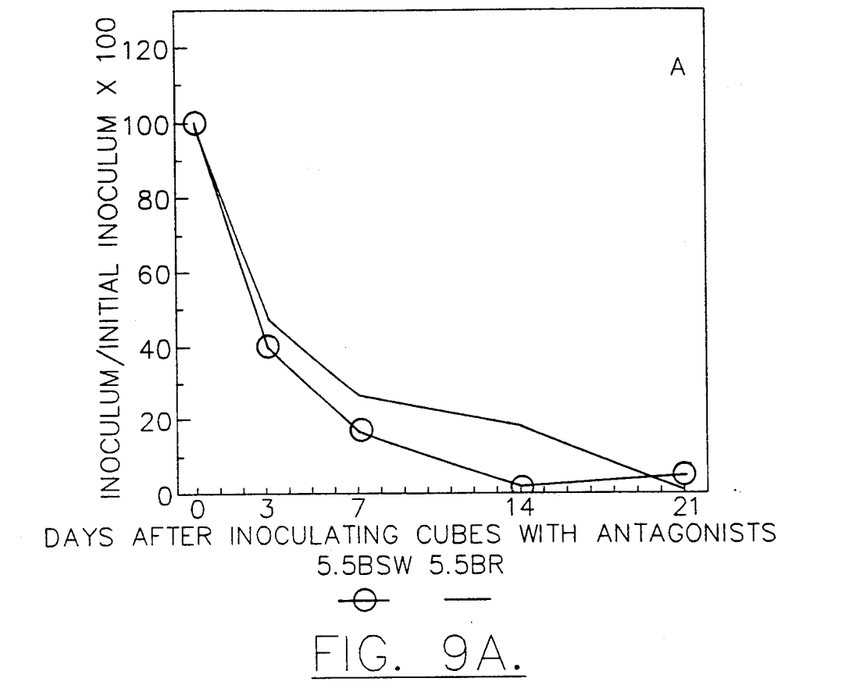
FIG. 9A is a plot of *P. cepacia* population survival rate as a function of time in root cubes infested with *R. solani* for subcultured samples and rifampicin-resistant samples of *P. cepacia.*
Figure 9B:
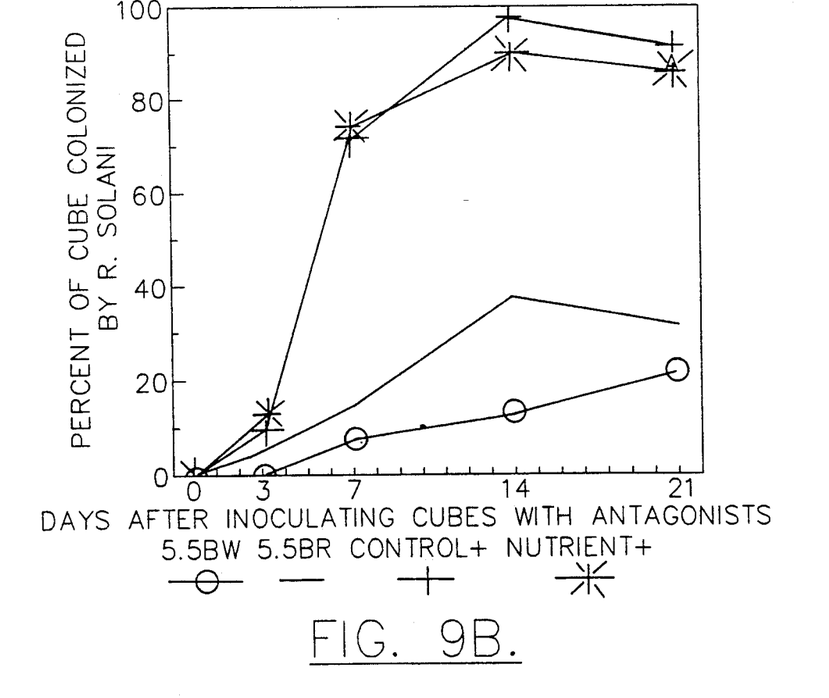
Figure 10A:
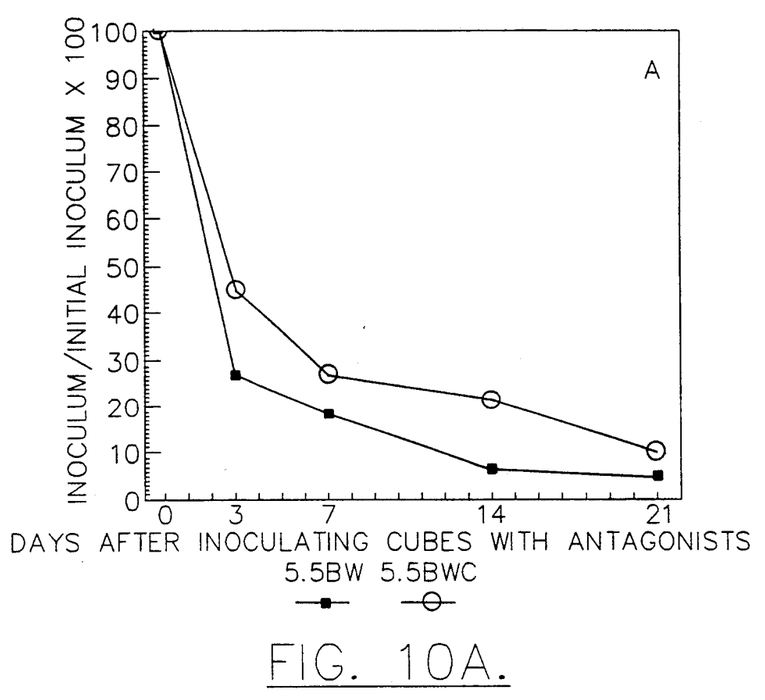
Figure 10B:
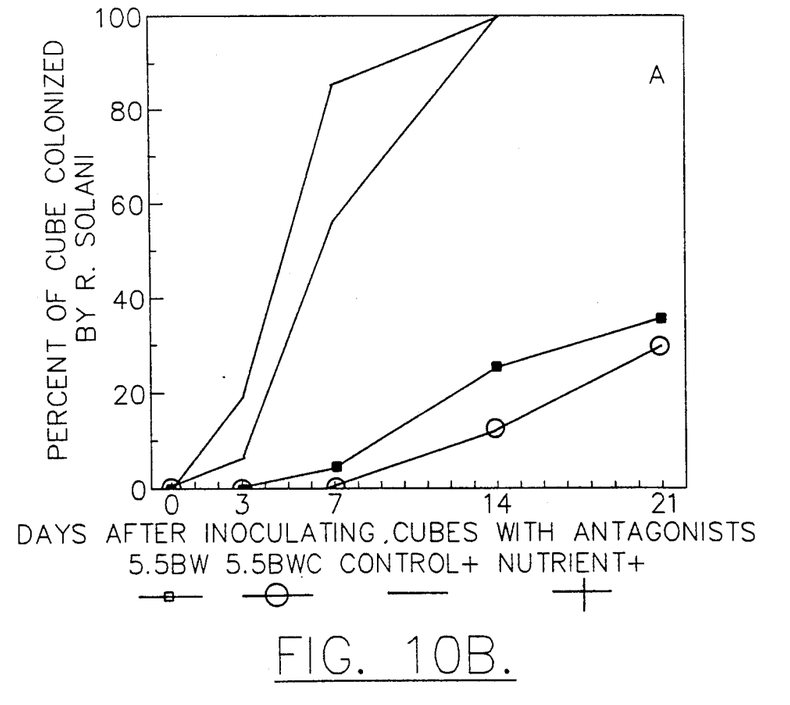

Colonization of the rooting cubes by R. solani was determined in the antagonist treated cubes and the infested, untreated controls as follows: the outer 3 mm of a half. cube was aseptically removed, leaving a cube approximately $15 \times 20 \times 27$ mm in size. This was then aseptically dissected into four sections from the outside to the middle. Each section measured about $15 \times 5 \times 27$ mm. These sections were then cut into nine uniform sections measuring $5 \times 5 \times 9$ mm. A total of 36 sections per half cube were assayed for the presence of R. solani. Sections were placed on AWPDA. Sections were observed for presence of R. solani 24 hr later. A numbering system of the sections was included to facilitate the monitoring of R. solani progress from the outside of the cube (where rice grain infested with R. solani is placed) towards the middle of the cube (where the cutting is). Data presented in Examples 12-14 is based on colonization of entire cube or only the top 9 mm of the cube. Data collected in this procedure is described in Example 12 (FIGS. 8A and 8B), Example 13 (FIGS. 9A and 9B), and Example 14 (FIGS. 10A and 10B).

EXAMPLE 12

Influence of Inoculum Source on Population Dynamics

Figure 8A:
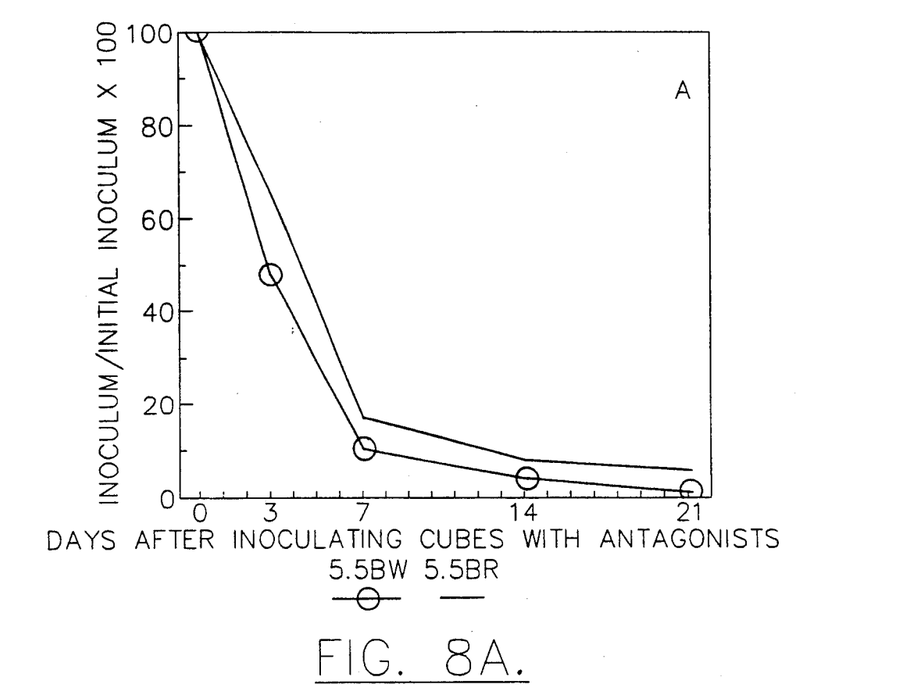
FIG. 8A is a plot of *P. cepacia* population survival rate as a function of time root cubes infested with *R. solani*.

Cubes were prepared and testing was carried out in accordance with the procedure described in Example 11. The population of isolate 5.5B varied slightly based on source of inoculum. Reduction of 5.5B population was typically rapid after only three days. In this trial, 52, 89.1, 95.1, and 98% reduction in 5.5BW population occurred after three, seven, 14, and 21 days. During the same periods, 34.2, 82.6, 91.5, and 93.7% reduction in 5.5BR occurred (FIG. 8A). A total of three plants became infected in cubes treated with 5.5BW over the three week period, while a total of eight plants were infected in the 5.5BR treated cubes.

Figure 8B:
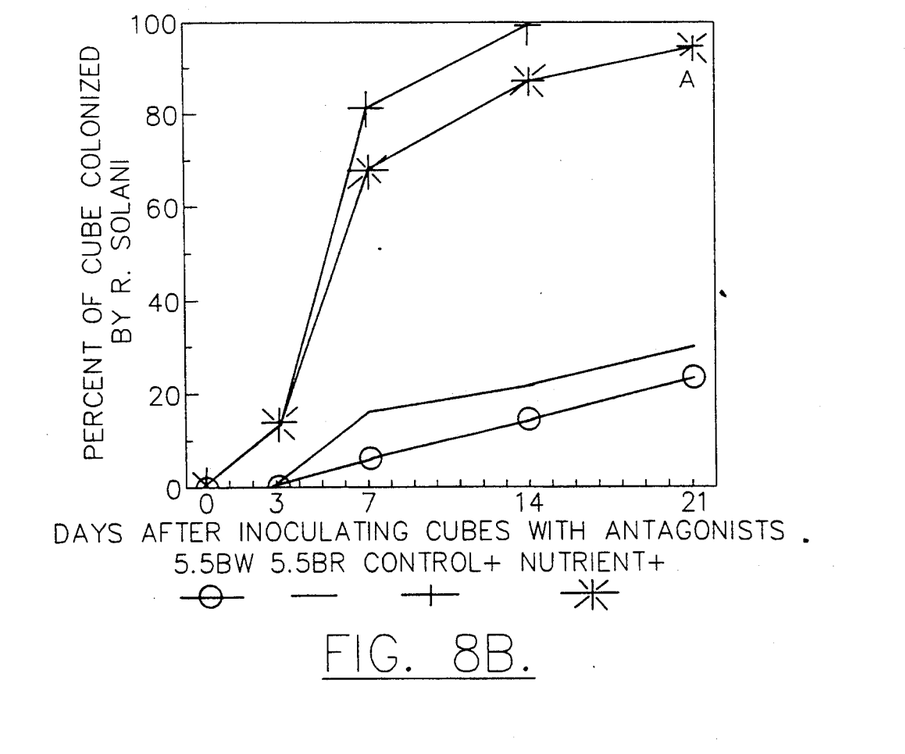
FIG. 8B is a plot of *R. solani* colonization as a function of time on the entirety of root cubes inoculated with *P. cepacia* and untreated cubes.

Colonization by R. solani was greatest in the 5.5BR treated cubes where 0, 16.7, 22, and 30.5% of the cube was colonized after three, seven, 14, and 21 days. Comparatively, only 0, 6.25, 14.5, and 23% of the 5.5B treated cubes were colonized (FIG. 8B). In the infested controls, 95.1 (nutrient) and 100% (water) of the cube was colonized after 21 days. The top 9 mm of the cube was rapidly colonized by R. solani in both treatments, with more colonization in the 5.5BR treatment (data not shown). After 21 days, 81.3 and 64.5% of the top of the 5.5BR and 5.5BW treated cubes were colonized by R. solani.

EXAMPLE 13

Influence of Subculturing and Rifampicin on Population Dynamics

Cubes were prepared as described in Example 11. Reduction in population of 5.5BR and 5.5BSW treatments was rapid after three days. After three, seven, 14, and 21 days, 60, 82.9, 98.2, and 94.8% reduction in population of 5.5BSW had occurred. In the 5.5BR treated cubes, population declined by 52.2, 73, 81.6, and 98.7%, respectively (FIG. 9A). Four plants became infected in cubes treated with 5.5BSW over the three week period, while 12 plants became infected in the 5.5BR treated cubes.

Colonization by R. solani was greatest in the 5.5BR treated cubes with 5.5, 15.2, 38.2 and 31.9% of the cube colonized after three, seven, 14, and 21 days. In the 5.5BSW treated cubes, only 0, 7.6, 13.2, and 22.2% of the cubes were colonized after three, seven, 14, and 21 days (FIG. 9B). In the infested controls, 87% (nutrient) and 92.4% (water) of the cubes were colonized after 21 days. Only 54.2% of the 5.5BSW treated cubes were colonized in the top 9 mm after 14 days compared to 100 percent colonization for the 5.5BR treated cuttings (data not shown). In the infested controls, 100% colonization by R. solani occurred in the top 9 mm after seven days. The greater colonization of the cubes, especially in the top of the cubes, seems to correlate well with the increased occurrence of infection based on results with 5.5BR treatments while less colonization, as mentioned, with the 5.5BSW treatments resulted in greater efficacy of control.

EXAMPLE 14

Influence of Storage Temperature on Population Dynamics

Cubes were prepared and testing was carried out in accordance with the procedure described in Example 11.

In this trial, inoculum was produced by growing cultures seeded from cultures of 5.5B stored in sterile water at 20° C. (5.5BW) or 4° C. (5.5BWC). Population reduction of 5.5BW was 72.9, 81.6, 93.3, and 95% after three, seven, 14, and 21 days while reductions of 55.1, 72.8, 78.3, and 89.8% occurred with the population of 5.5BWC during the same time periods (FIG. 10A). Seven plants became infected in the 5.5BW treated cubes while five were diseased in the 5.5BWC cubes.

Colonization of the cubes by R. solani was greatest in the 5.5BW treated cubes where 0, 4.86, 25.7, and 36.1% of the cubes were colonized after three, seven, 14, and 21 days. In the 5.5BWC treated cubes, 0, 0, 12.5, and 29.9% of the cubes were colonized after three, seven, 14, and 21 days (FIG. 10B). In both infested controls, 100% colonization of the cubes occurred after 21 days.

Colonization of the top of the cube was 95.8 and 66.7% for cubes treated with isolate 5.5BW and 5.5BWC, respectively (data not shown). After seven and 14 days, 100% of the top of the cubes was colonized in both the infested nutrient and the water controls. This slower decline in population of 5.5BWC seems to correlate with the lack of colonization and greater efficacy of control. This compares favorably to isolate 5.5BW, which suffered a more rapid decline in population, possibly allowing the R. solani to colonize (especially the top of the cube) the cube late in the experiment and thereby infecting a greater percentage of cuttings.

The foregoing examples are illustrative of the present invention, and are not to be construed as limiting thereof. The invention is defined by the following claims, with equivalents of the claims to be included therein.

That which is claimed is:

1. A biologically pure culture of *Pseudomonas cepacia* strain having all of the identifying characteristics of *Pseudomonas cepacia* NCSU strain 5.5B (ATCC 55344).

* * * * *